United States Patent [19]

Roman

[11] Patent Number: 6,110,474
[45] Date of Patent: *Aug. 29, 2000

[54] COSMETIC COMPOSITIONS CONTAINING A COFFEE EXTRACT PIGMENT

[75] Inventor: Frank Roman, Garden City, N.Y.

[73] Assignee: E-L Management Corp., New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/856,621

[22] Filed: May 13, 1997

[51] Int. Cl.$^7$ .............................. A61K 6/00; A61K 7/00; A45D 40/26

[52] U.S. Cl. ............................ 424/401; 424/401; 424/63; 424/69; 132/320; 514/547; 514/844

[58] Field of Search ................................. 424/401, 63, 69; 132/320; 514/847, 844

[56] References Cited

U.S. PATENT DOCUMENTS

| | | | |
|---|---|---|---|
| 3,980,089 | 9/1976 | Pittet et al. | 131/144 |
| 4,324,704 | 4/1982 | Trenkle et al. | 252/522 R |

*Primary Examiner*—John Kight
*Assistant Examiner*—D. Faulkner
*Attorney, Agent, or Firm*—Karen A. Lowney, Esq.

[57] ABSTRACT

The present invention relates to a pigment composition comprising an effective amount of an aqueous extract of coffee and at least one organic pigment. The pigment compositions are useful in preparing cosmetic formulations in which a true black color in the final product is needed. In particular, the pigment composition is useful in the preparation of eyeliner, lash coloring, and hair dyes or rinses.

21 Claims, No Drawings

COSMETIC COMPOSITIONS CONTAINING A COFFEE EXTRACT PIGMENT

FIELD OF THE INVENTION

The present invention relates to cosmetic compositions containing natural products as pigments. More specifically, the invention relates to cosmetic compositions containing coffee extract as pigment.

BACKGROUND OF THE INVENTION

Traditionally, the pigments of choice for dark eye makeup, particularly eyeliner and mascara, have been inorganic oxides, for example, iron oxide or titanium dioxide. Although these pigments are capable of producing the darkest desirable shades, in particular, a true black, these materials come in the form of large particles. This form can be cumbersome to work with, in particular when forming a product which is intended to go on in liquid form through a narrow applicator. For example, in a typical eyeliner "pen", the oxide particles have a tendency to clog the nib of the pen, so that the liquid eyeliner does not flow smoothly, or at all, through the nib and onto the skin. In addition, even if flow should continue, the black pigment will tend to be filtered out, thereby diluting the color to an off-brown.

More recently, a group of organic pigments, namely D&C and FD&C pigments, have also been used in the preparation of cosmetics in which a dark color is desirable. The advantage of these pigments is that they do not have the large particulate form of the inorganic pigments; however, the major limitation of these pigments is that they are incapable of producing a true black color. In the present context, "true black" is defined as the absolute non-reflectance of color, i.e., a reading on a spectrophotometer of less than 4.75. The inability to make a true black with organic pigments is a serious drawback in attempting to make a typical eyeliner or mascara, and therefore, limits the utility of these materials.

There is thus still a need for pigment which can provide the desired black or very dark colors for use in eyeliner and mascara, and yet which will be easily adaptable to a liquid eyeliner formulation. The present invention provides a useful alternative to the traditionally used pigments for eye products.

SUMMARY OF THE INVENTION

The present invention relates to pigment composition comprising an effective amount of an aqueous extract of coffee and at least one organic pigment. By "effective amount" in the present context is meant an amount sufficient to confer a dark, nearly black, color to the resulting pigment composition. The invention further relates to cosmetic compositions containing the pigment combination. The pigment composition has the advantage not only of providing a true black color, but also providing a substantial measure of indelibility to cosmetic compositions containing them. In one embodiment, the pigment composition is intended for use in the eye area. For example, the composition is a lash color, which when applied to lashes, provides a long lasting, substantially indelible color, which will not wear off naturally, but must be actively removed with soap and water. In another example, the composition is an eyeliner, preferably a liquid eyeliner, which also provides an indelible color to the eyelid. The pigment can also be used alone as a hair dye or combined with other natural hair dyes, such as henna, to make a darker natural hair rinse than has heretofore been available.

DETAILED DESCRIPTION OF THE INVENTION

Coffee extracts of various types have been previously used in cosmetic formulations. For example, JP 7101881 discloses cosmetic compositions in which natural colorants based on extracts from coffee are bound with hemicellulose and whey, presumably to stabilize the product. SU 1799593 discloses a castor oil-based lipstick containing a UV filter consisting of coffee fat and oil extract. JP 89018043 discloses a cosmetic material which employs roasted powdered coffee, or an extract thereof, as a scrubbing agent. However, its use in an eye product or hair dye has not previously been disclosed, nor has its combination with FD&C pigments.

The coffee extract of the invention is prepared as an aqueous extract from a dark roast coffee, for example, from a French roast, Italian roast or espresso roast, the latter being particularly preferred. The extract can be prepared by mixing boiling water with ground coffee beans. An effective mixture is approximately 80% water, by weight, and 20% coffee grounds, although the amount of coffee used can range from about 20–40% of the total mixture. The coffee and water are mixed well for at least about 5 minutes, then the mixture is strained to remove the remaining grounds. The resulting extract can be stored at room temperature, but if to be kept stored for long periods, a preservative should be added.

The coffee extract thus prepared is incorporated into a cosmetic base appropriate for the purpose for which the final product is intended. The amount of extract used is not critical, but assuming, as an example, a 20% coffee extract, generally, the extract will constitute at least about 10% by weight of the total cosmetic composition in which it is to be used, preferably at least about 15%, and most preferably at least about 18%. However, in most cases, the coffee extract will be first combined with at least one other organic pigment to form a pigment composition which is then incorporated into the cosmetic base.

In one such embodiment, the coffee extract is combined with at least one D&C or FD&C pigment. These are routinely available color additives which are enumerated, for example, in International Cosmetic Ingredient Handbook, Third Edition, 1996. Certain of these pigments, namely FD&C Blue No.1, FD&C Red No. 40, and FD&C Yellow #5 are currently permitted in the eye area, and therefore, when the pigment composition is to be used in a product for the eye area, as, for example, in a lash color or eyeliner, these pigments are preferred. In the preparation of an eyeliner composition, the pigment composition is utilized in an aqueous base. The solvent employed is an aqueous solvent, preferably water, or a combination of water and alcohol; preferably, the alcohol is a glycol, for example, butylene glycol. To obtain a true black color, the preferred components are FD&C Blue No. 1, FD&C Red No. 40, and coffee extract, each in approximately equal amounts, i.e., each component pigment preferably being present in an amount which varies no more than about ±20–30% of the amount one of the other pigment components. The absolute amounts of the components are not critical, however, as the pigment composition will be diluted to the desired concentration in preparation of the final product, typically resulting in a final concentration of from about 1–15%, more preferably about 2–10%, of each pigment in the final product. To obtain other dark colors, the amounts can be varied depending upon the intensity of color desired; the skilled artisan will immediately recognize how these combinations can be optimized to achieve the desired color. If the pigment composition is not to be used in the eye area, it is possible to use FD&C and D&C colors other than those which are specifically approved for use near the eye. It is also possible to combine the coffee extract with other naturally occurring pigments, such as chlorophyll, carotenoids, saffron, beet extract, paprika, or carmine.

In certain embodiments, the pigments of the composition are combined with an emulsifier/surfactant to aid in dispersion. Among the useful emulsifier/surfactants which can be used for this purpose are fatty alcohol-derived emulsifiers, such as polyoxyethylene fatty acid ethers, or alkyl sulfates, preferably in an amount of from about 1–20%. The pigment composition is then combined with one or more film-forming agents, such as PVP-based polymers, acrylate-based copolymers, silicone-based films, or organic film-formers, such as starch, cellulose or gums, in an amount of from about 0.25–20%, the specific amount being determined based on the nature of the end product. In the eyeliner, for example, only small amounts of film-former, usually less than 1%, will be employed so as to avoid hampering flowability through a pen nib; on the other hand, for application to hair and lashes, the amount used can be increased significantly. Optionally, a small amount of preservative, usually less than 1%, preferably less that 0.5%, by weight of the total composition, is included.

In the embodiment in which the extract is used in a lash coloring composition, the texture of the final product will differ somewhat from that of an eyeliner. For proper application and adherence to the lashes, the product must be of a pasty or creamy consistency. To that end, the composition, in addition to those components listed above, will also contain one or more viscosifying agents to thicken the texture of the composition. The viscosifying agents can be selected from, for example, carbomers, hectorites, gums, celluloses, waxes, alginates, carageenans, starches or silicates, typically in an amount of about 0.005–5%.

The present pigment compositions provide a significant advantage over other pigment combinations used in the eye area. The use in an eyeliner composition is particularly advantageous because the product can be used directly in a flow-through pen, to produce a true black color, without any risk of clogging or blockage. While other non-flow-through pens are available, which pens can use the particle-based pigments, these frequently require the use of pumps or bulbs to push the product through the nib. Moreover, because of the particle size, the nib is necessarily fairly wide to accommodate them. Unfortunately, a wide nib is not conducive to accurate, subtle application of liner on the lid, and is therefore not favored by consumers. In contrast, with the present pigment composition, the resulting eyeliner formulation flows easily through a very narrow nib, giving an accurate, elegant line; it also has the added advantage of using organic pigments, and being long-wearing, in fact, substantially indelible, until removed with soap and water. Thus, an additional embodiment of the present invention is a flow-through type eyeliner pen containing an eyeliner composition comprising the subject pigment composition.

With respect to a lash product, the formulation provides a unique coloring mechanism for the lashes without the necessity for application of a heavy coat of mascara. Here, as with the eyeliner, the color is substantially indelible, giving the desirable appearance of darker lashes, even after the applied product has worn off, without a heavy, made-up appearance, and without the necessity for repeated applications during the day. Thus, the present invention also provides an eyelash coloring applicator, the applicator comprising a base containing the lash coloring formulation, and a cap comprising a wand containing means for applying the formulation to the eyelashes, which cap is inserted removably into the base.

In addition to eye products, the pigment compositions can also be used in any cosmetic product in which it is desirable to provide a dark or black color. For example, the pigment is useful in hair coloring compositions, such as hair rinses, to provide an organic hair color which is long lasting but will not damage hair. In one such embodiment, the pigment composition is combined with henna. An advantage to this combination is the additional variety of shades available with a henna rinse, while providing a natural, gentle coloring rinse. A powdered henna pigment can be combined with the coffee extract in the same manner as described above for the organic pigments, and processed accordingly. The pigment compositions of the invention, whether with henna or other organic pigments, can also be used to streak hair, or as a comb-in or rinse covering for grey hair.

The invention is further illustrated by the following non-limiting examples.

EXAMPLES

Example I

Preparation of a Coffee Extract

A dark roast espresso coffee is ground in a standard household coffee grinder to a fineness suitable for brewing espresso coffee. To make a 20% coffee extract base, deionized water is weighed out and heated to boiling. An amount of coffee grounds sufficient to give a 20% mixture is added to the water, and mixed well for five minutes. The mixture is then strained through a drip coffee paper filter and stored at room temperature until ready for use.

Example II

Preparation of a Pigment Composition

A 40% D&C Red No.40 base is prepared as follows: Butylene glycol(Hoechst Celanese) is weighed out and combined with sufficient FD&C Red No. 40 to give a 40% (by weight) mixture. The components are mixed well, until the pigment is thoroughly wetted. The mixture is then ground twice through a triple roller mill, collected and stored at room temperature until further use. Using the same procedure, a 30% eD&C blue base is also prepared.

The organic pigments and the coffee extract components are mixed with a solvent appropriate for the end use, and combined with the remaining ingredients of the cosmetic composition.

Example III

Preparation of an Organic Eyeliner

A black liquid eyeliner having the following composition is prepared:

| COMPONENT | % BY WEIGHT |
| --- | --- |
| Pigment base | |
| Oleth-20(Croda, Inc.) | 10.5 |
| FD&C Red No. 40(40% in butylene glycol) | 10.5 |
| FD&C Blue No. 1(30% in butylene glycol) | 18.4 |
| Chlorophyll(1% in water) | 10.5 |
| Coffee extract(20% in water) | 18.4 |
| Preservative base | |
| Deionized water | Q.S. |
| TEA-Lauryl sulfate (Henkel) | 1.5 |
| Oleic acid | 1.5 |

-continued

| COMPONENT | % BY WEIGHT |
|---|---|
| phenoxyethanol | 0.3 |
| Na3EDTA | 0.02 |
| methylparaben | 0.4 |
| propylparaben | 0.13 |
| butylparaben | 0.13 |
| Film formers | |
| Acrylates copolymer (Goodrich) | 0.53 |
| PVP/polycarbamyl polyglycol ester (Phoenix) | 0.53 |

To prepare the pigment component, the solvent is weighed out and the pigments are added into the solvent and mixed thoroughly until dissolved, and then strained through a fine mesh cloth.

The preservative base components are mixed together as follows: the deionized water is weighed out, and the Na3EDTA sprinkled in, and mixed well under a Silverson homogenizer at 3600 rpm; this mixture is then heated to 70° C. and mixed for five minutes. The parabens are added and the mixing continued for an additional ten minutes, while maintaining the temperature at 70° C. The speed of the mixing is then reduced to about 2500 rpms and the TEA-lauryl sulfate is added to the mixture. The oleic acid and phenoxyethanol are weighed out separately, mixed well and heated to 72° C. These are then added to the water mixture, and mixed under a homogenizer at medium speed for fifteen minutes. The homogenizer is removed, sweep blades put on, and mixing continued until emulsion reaches 30° C., then the mixture is discharged.

For final preparation, the preservative base is added to the pigment mixture, and blended thoroughly. The two film-forming agents are then added and mixed well. The mixture is then discharged and stored.

Example IV

Preparation of an Organic Lash Color

A lash coloring product having the following composition is prepared:

| COMPONENT | % BY WEIGHT |
|---|---|
| Preservative Base | |
| Deionized water | Q.S. |
| Butylene glycol | 0.6 |
| Xanthan gum(Calgon) | 0.1 |
| Methylparaben | 0.15 |
| Propylparaben | 0.05 |
| Butylparaben | 0.05 |
| Na3EDTA | 0.08 |
| TEA-lauryl sulfate (Henkel) | 0.6 |
| Oleic acid | 0.6 |
| Phenoxyethanol | 0.11 |
| Pigment base | |
| ethoxydiglycol (Gattefosse s.a.) | 10.0 |
| FD&C Blue No. 1(30% in butylene glycol) | 15.0 |
| FD&C Red No. 40(40% in butylene glycol) | 15.0 |
| Chlorophyll(1% in water) | 10.0 |
| Coffee extract(20% in water) | 20.0 |
| Conditioner | |
| Tricaprylin(Trivent OC-G) | 3.0 |

-continued

| COMPONENT | % BY WEIGHT |
|---|---|
| Film formers | |
| Acrylates copolymer (Goodrich) | 7.5 |
| PVP/polycarbamyl polyglycol ester(Phoenix) | 7.5 |

The pigment base is prepared substantially as described above. The preservative base is prepared as follows: Deionized water is weighed out. Separately, butylene glycol and xanthan gum are weighed out, and mixed well together until the gum is completely wetted. This mixture is then added to the water under a homo mixer at slow speed; The parabens are added and mixed for 15 minutes. The mixing speed is lowered and the TEA-Lauryl sulfate added. The materials are mixed for 10 minutes, and heated to 70° C. The oleic acid and phenoxyethanol are weighed out separately, and heated to 72° C, then added to the water mixture. The mixing speed is increased to medium and mixing continued for fifteen minutes. The homogenizer is removed, sweep blades put on, and mixing continued until the emulsion reaches 30° C., then the mixture is discharged.

To prepare the final product, the pigment base components, the conditioner, and the preservative base are combined and mixed well until all colors are completely dissolved. Ethoxydiglycol is added and mixed in well. The film-forming agents are then added, and the mixture vigorously blended until thick and uniform.

Example V

Evaluation of Blackness of Pigment Composition

An eyeliner composition prepared as described above is tested to determine on a spectrophotometer its % reflectance of light over a range of wavelengths. At wavelengths between 400 and 640 λ, the composition measures below 4.75% reflectance, this standard being the measurement of a true black. The pigment composition is also tested against carbon black and a typical black oxide pigment. The eyeliner registers as being blacker than the black oxide and substantially as black as carbon black.

What we claim is:

1. A pigment composition comprising an aqueous extract of coffee and at least one organic pigment.

2. The composition of claim 1 in which the coffee extract is combined with at least one D&C or FD&C pigment.

3. The composition of claim 2 which comprises FD&C Red No. 40, FD&C Blue No. 1.

4. The composition of claim 3 in which the composition produces a true black color.

5. The composition of claim 2 which comprises an additional organic pigment.

6. The composition of claim 5 in which the additional pigment is chlorophyll.

7. The composition of claim 1 in which the organic pigment comprises henna.

8. The pigment composition of claim 1 which also comprises an aqueous solvent.

9. The composition of claim 8 in which the solvent is a hydroalcoholic solvent.

10. The composition of claim 9 in which the solvent is a glycol.

11. The composition of claim 10 in which the solvent is butylene glycol.

12. The composition of claim 8 which also comprises a surfactant.

13. A cosmetic formulation comprising a aqueous extract of coffee and at least one organic pigment, and a cosmetically acceptable vehicle.

14. The formulation of claim 13 in which the organic pigment is a D&C or FD&C pigment.

15. The formulation of claim 14 which comprises FD&C Red No. 40 and FD&C Blue No. 1.

16. The formulation of claim 15 which further comprises at least one film forming agent.

17. The formulation of claim 16 which is a lash composition.

18. The formulation of claim 17 which further comprises at least one viscosifying agent.

19. The formulation of claim 15 which is an eyeliner.

20. The formulation of claim 13 which is a hair rinse comprising an henna.

21. A flow-through eyeliner pen containing an eyeliner formulation comprising a aqueous extract of coffee and at least one organic pigment.

* * * * *